United States Patent [19]
Hagen et al.

[11] Patent Number: 6,160,186
[45] Date of Patent: Dec. 12, 2000

[54] PREPARATION OF POLYOXYMETHYLENE DIMETHYL ETHERS BY CATALYTIC CONVERSION OF DIMETHYL ETHER WITH FORMALDEHYDE FORMED BY DEHYDROGENATION OF DIMETHYL ETHER

[75] Inventors: Gary P. Hagen, West Chicago; Michael J. Spangler, Sandwich, both of Ill.

[73] Assignee: BP Amoco Corporation, Chicago, Ill.

[21] Appl. No.: 09/191,399

[22] Filed: Nov. 12, 1998

[51] Int. Cl.$^7$ ................................................. C07C 43/11
[52] U.S. Cl. .................... 568/613; 568/618; 568/621; 568/485
[58] Field of Search ....................... 568/618, 613, 568/621, 485; 252/182.12; 44/447, 448

[56] References Cited

U.S. PATENT DOCUMENTS

| | | | |
|---|---|---|---|
| 2,449,469 | 9/1948 | Gresham et al. | 260/615 |
| 2,663,742 | 12/1953 | Frevel et al. | 260/615 |
| 2,882,243 | 4/1959 | Milton | 252/455 |
| 2,882,244 | 4/1959 | Milton | 252/455 |
| 3,130,007 | 4/1964 | Breck | 23/113 |
| 3,702,886 | 11/1972 | Argauer et al. | 423/328 |
| 3,709,979 | 1/1973 | Chu | 423/328 |
| 3,832,449 | 8/1974 | Rosinski et al. | 423/328 |
| 4,014,939 | 3/1977 | Osugi et al. | 260/603 R |
| 4,054,609 | 10/1977 | Osugi et al. | 260/603 R |
| 4,215,011 | 7/1980 | Smith | 252/426 |
| 4,268,420 | 5/1981 | Klotz | 252/432 |
| 4,269,813 | 5/1981 | Klotx | 423/277 |
| 4,292,457 | 9/1981 | Klotz | 585/469 |
| 4,292,458 | 9/1981 | Klotz | 585/469 |
| 4,341,069 | 7/1982 | Bell et al. | 60/39.02 |
| 4,354,045 | 10/1982 | Merger et al. | 568/487 |
| 4,443,559 | 4/1984 | Smith, Jr. | 502/527 |
| 4,967,014 | 10/1990 | Masamoto et al. | 568/458 |
| 5,113,015 | 5/1992 | Plamer et al. | 562/608 |
| 5,746,785 | 5/1998 | Moulton et al. | 44/443 |

FOREIGN PATENT DOCUMENTS

| | | |
|---|---|---|
| 25207 | 9/1984 | Australia . |
| 245868 | 5/1987 | Germany . |
| 688 041 | 4/1997 | Switzerland . |

*Primary Examiner*—Johann Richter
*Assistant Examiner*—Rosalynd Keys
*Attorney, Agent, or Firm*—Frederick S. Jerome; Robert A. Yesukevich

[57] ABSTRACT

A particularly useful process which includes the steps of providing a source of formaldehyde formed by conversion of dimethyl ether in the presence of a catalyst comprising copper and zinc; and contacting the source of formaldehyde and a predominately dimethyl ether feedstream with a heterogeneous, condensation promoting catalyst capable of hydrating dimethyl ether under conditions of reaction sufficient to form an effluent comprising water, methanol, formaldehyde, dimethyl ether, and polyoxymethylene dimethyl ethers is disclosed. Unreacted dimethyl ether is recovered from the effluent and recycled to the formation of polyoxymethylene dimethyl ethers. The resulting dimethyl ether-free liquid mixture is heated in the presence of an acidic catalyst to convert at least the methanol and formaldehyde present to polyoxymethylene dimethyl ethers. Advantageously, methylal and higher polyoxymethylene dimethyl ethers are formed and separated in a catalytic distillation column. By including in the column an anion exchange resin, an essentially acid-free product is obtained which can be used directly as a blending component, or fractionated, as by further distillation, to provide more suitable components for blending into diesel fuel.

21 Claims, 1 Drawing Sheet

PREPARATION OF POLYOXYMETHYLENE DIMETHYL ETHERS BY CATALYTIC CONVERSION OF DIMETHYL ETHER WITH FORMALDEHYDE FORMED BY DEHYDROGENATION OF DIMETHYL ETHER

TECHNICAL FIELD

The present invention relates to production of organic compounds, particularly polyoxymethylene dimethyl ethers, which are suitable components for blending into fuel having improved qualities for use in diesel engines. More specifically, it relates to employing a heterogeneous, condensation promoting catalyst capable of hydrating dimethyl ether in conversion of dimethyl ether and formaldehyde to form a condensation effluent. A dimethyl ether-free mixture, separated form the effluent, is heated in a catalytic distillation column to convert methanol and formaldehyde present to methylal and higher polyoxymethylene dimethyl ethers and separate the methylal from the higher polyoxymethylene dimethyl ethers. Advantageously, the catalytic distillation column has a section containing an anion exchange resin whereby an essentially acid-free product is obtained which can be used directly as a blending component, or fractionated, as by further distillation, to provide more suitable components for blending into diesel fuel.

This integrated process also provides its own source of formaldehyde which is an un-purified liquid stream derived from a mixture formed by dehydrogenation of dimethyl ether using a catalyst based on copper, zinc and a member selected from the group consisting of sulfur, selenium and tellurium as catalyst components.

BACKGROUND OF THE INVENTION

Conversion of low molecular weight alkanes such as methane to synthetic fuels or chemicals has received increasing attention because low molecular weight alkanes are generally available from secure and reliable sources. For example, natural gas wells and oil wells currently produce vast quantities of methane. Reported methods for converting low molecular weight alkanes to more easily transportable liquid fuels and chemical feedstocks can be conveniently categorized as direct oxidative routes and/or as indirect syngas routes. Direct oxidative routes convert lower alkanes to products such as methanol, gasoline, and relatively higher molecular weight alkanes. In contrast, indirect syngas routes typically involve production of synthesis gas as an intermediate product.

Routes are known for converting methane to dimethyl ether. For example, methane is steam reformed to produce synthesis gas. Thereafter, dimethyl ether and methanol can be manufactured simultaneously from the synthesis gas, as described in U.S. Pat. No. 4,341,069 issued to Bell et al. They recommend a dimethyl ether synthesis catalyst having copper, zinc, and chromium co-precipitated on a gamma-alumina base. Alternatively, methane is converted to methanol, and dimethyl ether is subsequently manufactured from methanol by passing a mixed vapor containing methanol and water over an alumina catalyst, as described in an article by Hutchings in New Scientist (Jul. 3, 1986) 35.

Formaldehyde is a very important intermediate compound in the chemical industry. The extreme reactivity of the formaldehyde carbonyl group and the nature of the molecule as a basic building block has made formaldehyde an important feedstock for a wide variety of industrially important chemical compounds. Historically, formaldehyde has found its largest volume of application in the manufacture of phenol-formaldehyde resins, urea-formaldehyde resins and other polymers. Pure formaldehyde is quite uncommon since it polymerizes readily. It was usually obtained as an aqueous solution such as formalin, which contains only about 40 percent formaldehyde. However, more recently, formaldehyde is usually transported as an item of commerce in concentrations of 37 to 50 percent by weight. A solid source of formaldehyde called paraformaldehyde is also commercially available.

Because of the reactivity of formaldehyde, its handling and separation require special attention. It is a gas above −19° C. and is flammable or explosive in air at concentrations of about 7 to about 12 mol percent. Formaldehyde polymerizes with itself at temperatures below 100° C. and more rapidly when water vapor or impurities are present. Since formaldehyde is usually transported in aqueous solutions of 50 percent by weight or lower concentration, producers have tended to locate close to markets and to ship the methanol raw material, which has a smaller volume.

It is known that some reactions may be carried out by means of catalytic distillation. In catalytic distillation, reaction and separation are carried out simultaneously in a distillation column with internal and/or external stages of contact with catalyst.

In U.S. Pat. No. 4,215,011, Smith, Jr. discloses a method for the separation of an isoolefin, preferably having four to six carbon atoms, from streams containing mixtures thereof with the corresponding normal olefin, wherein the mixture is fed into a reaction-distillation column containing a fixed-bed, acidic cation exchange resin and contacted with the acidic cation exchange resin to react the isoolefin with itself to form a dimer and the dimer is separated from the normal olefin, the particulate catalytic material, i.e., the acidic cation exchange resin, being contained in a plurality of closed cloth pockets, which pockets are arranged and supported in the column by wire mesh.

In U.S. Pat. No. 4,443,559, Smith, Jr. discloses a catalytic distillation structure which comprises a catalyst component associated intimately with or surrounded by a resilient component, which component is comprised of at least 70 vol. percent open space for providing a matrix of substantially open space. Examples of such resilient component are open-mesh, knitted, stainless wire (demister wire or an expanded aluminum); open-mesh, knitted, polymeric filaments of nylon, Teflon, etc.; and highly-open structure foamed material (reticulated polyurethane).

In U.S. Pat. No. 5,113,015, David A. Palmer, K. D. Hansen and K. A. Fjare disclose to a process for recovering acetic acid from methyl acetate wherein the methyl acetate is hydrolyzed to methanol and acetic acid via catalytic distillation.

In German Democratic Republic DD 245 868 A1 published May 20, 1987 in the text submitted by the applicant, preparation of methylal is carried out by reaction of methanol with trioxane, formalin or paraformaldehyde in the presence of a specific zeolite. Autoclave reactions of 1 to 8 hours are described using a zeolite of the "LZ40 type" with a ratio of silicon dioxide to alumina ratio of 78 at temperatures from 493 to 543 K. Methylal content of the product as high as 99.8 percent (without methanol) is reported for trioxane at 523 K for 3 hours. Reaction pressures did not exceed 5 Mpa in the autoclave. Neither conversions nor selectivity are reported.

In U.S. Pat. No. 4,967,014, Junzo Masamoto, Junzo Ohtake and Mamoru Kawamura describe a process for formaldehyde production by reacting methanol with formaldehyde to form methylal, CH₃OCH₂OCH₃, and then oxidizing the resulting methylal to obtain formaldehyde. In the methylal formation step, a solution containing methanol, formaldehyde and water was brought into solid-liquid contact with a solid acid catalyst, and a methylal-rich component was recovered as a distillate. This process employs reactive distillation performed using a distillation column and multireaction units. The middle portion of the distillation column was furnished with stages from which the liquid components were withdrawn and pumped to the reactor units, which contained solid acid catalyst. The reactive solutions containing the resulting methylal were fed to the distillation column, where methylal was distilled as the overhead product.

Polyoxymethylene dimethyl ethers are the best known members of the dialkyl ether polymers of formaldehyde. While diethyl and dipropyl polyoxymethylene ethers have been prepared, major attention has been given to the dimethyl ether polymers. Polyoxymethylene dimethyl ethers make up a homologous series of polyoxymethylene glycol derivatives having the structure represented by use of the type formula indicated below:

$$CH_3O(CH_2O)_nCH_3$$

Chemically, they are acetals closely related to methylal, CH₃OCH₂OCH₃, which may be regarded as the parent member of the group in which n of the type formula equals 1. They are synthesized by the action of methanol on aqueous formaldehyde or polyoxymethylene glycols in the presence of an acidic catalyst just as methylal is produced. On hydrolysis they are converted to formaldehyde and methanol. Like other acetals, they possess a high degree of chemical stability. They are not readily hydrolyzed under neutral or alkaline conditions, but are attacked by even relatively dilute acids. They are more stable than the polyoxymethylene diacetates.

Due to the relatively small differences in the physical properties (melting points, boiling points, and solubility) of adjacent members in this series, individual homologs are not readily separated. However, fractions having various average molecular weight values have been isolated. The normal boiling point temperature of a fraction having average n of 2 in the type formula is reported as 91° to 93° C. Boiling points at atmospheric pressure calculated from partial pressure equations range from 105.0° C. for n of 2, to 242.3° C. for n of 5. (Walker, Joseph Frederic, "Formaldehyde", Robert E. Krieger Publishing Co., issued as No. 159 of American Chemical Society Monograph series (1975), pages 167–169)

Polyoxymethylene dimethyl ethers are prepared in laboratory scale by heating polyoxymethylene glycols or paraformaldehyde with methanol in the presence of a trace of sulfuric or hydrochloric acid in a sealed tube for 15 hours at 150° C., or for a shorter time (12 hours) at 165° to 180° C. Considerable pressure is caused by decomposition reactions, which produce carbon oxides, and by formation of some dimethyl ether. The average molecular weight of the ether products increases with the ratio of paraformaldehyde or polyoxymethylene to methanol in the charge. A high polymer is obtained with a 6 to 1 ratio of formaldehyde (as polymer) to methanol. In these polymers, the n value of the type formula CH₃O(CH₂O)ₙCH₃ is greater than 100, generally in the range of 300 to 500. The products are purified by washing with sodium sulfite solution, which does not dissolve the true dimethyl ethers, and may then be fractionated by fractional crystallization from various solvents.

U.S. Pat. No. 2,449,469 in the names of W. F. Gresham and R. E. Brooks reported obtaining good yields of polyoxymethylene dimetbyl ethers containing 2 to 4 formaldehyde units per molecule. This procedure is carried out by heating methylal with paraformaldehyde or concentrated formaldehyde solutions in the presence of sulfuric acid.

In the past, various molecular sieve compositions, natural and synthetic, have been found to be useful for a number of hydrocarbon conversion reactions. Among these are alkylation, aromatization, dehydrogenation and isomerization. Among the sieves which have been used are Type A, X Y and those of the MFI crystal structure as shown in "Atlas of Zeolite Structure Types," Second Revised Edition, 1987, published on behalf of the Structure Commission of the International Zeolite Associates and incorporated by reference herein. Representative of the last group are ZSM-5 and AMS borosilicate molecular sieves.

Prior art developments have resulted in the formation of many synthetic crystalline materials. Crystalline aluminosilicates are the most prevalent and, as described in the patent literature and in the published journals, are designated by letters or other convenient symbols. Exemplary of these materials are Zeolite A (Milton, in U.S. Pat. No. 2,882,243), Zeolite X (Milton, in U.S. Pat. No. 2,882,244), Zeolite Y (Breck, in U.S. Pat. No. 3,130,007), Zeolite ZSM-5 (Argauer, et al., in U.S. Pat. No. 3,702,886), Zeolite ZSM-11 (Chu, in U.S. Pat. No. 3,709,979), Zeolite ZSM-12 (Rosinski, et al., in U.S. Pat. No. 3,832,449), and others.

It is well known that internal combustion engines have revolutionized transportation following their invention during the last decades of the 19th century. While others, including Benz and Gottleib Wilhelm Daimler, invented and developed engines using electric ignition of fuel such as gasoline, Rudolf C. K. Diesel invented and built the engine named for him which employs compression for autoignition of the fuel in order to utilize low-cost organic fuels. Development of improved diesel engines for use in automobiles has proceeded hand-in-hand with improvements in diesel fuel compositions, which today are typically derived from petroleum. Modern high performance diesel engines demand ever more advanced specification of fuel compositions, but cost remains an important consideration.

Even in newer, high performance diesel engines combustion of conventional fuel produces smoke in the exhaust. Oxygenated compounds and compounds containing few or no carbon-to-carbon chemical bonds, such as methanol and dimethyl ether, are known to reduce smoke and engine exhaust emissions. However, most such compounds have high vapor pressure and/or are nearly insoluble in diesel fuel, and they have poor ignition quality, as indicated by their cetane numbers. Furthermore, other methods of improving diesel fuels by chemical hydrogenation to reduce their sulfur and aromatics contents, also causes a reduction in fuel lubricity. Diesel fuels of low lubricity may cause excessive wear of fuel injectors and other moving parts which come in contact with the fuel under high pressures.

Recently, U.S. Pat. No. 5,746,785 in the names of David S. Moulton and David W. Naegeli reported blending a mixture of alkoxy-terminated poly-oxymethylenes, having a varied mixture of molecular weights, with diesel fuel to form an improved fuel for autoignition engines. Two mixtures were produced by reacting paraformaldehyde with (i) methanol or (ii) methylal in a closed system for up to 7 hours and at a temperatures of 150° to 240° C. and pressures of 300 psi to 1,000 psi to form a product containing methoxy-terminated poly-oxymethylenes having a molecular weight of from about 80 to about 350 (polyoxymethylene dimethyl ethers). More specifically, a 1.6 liter cylindrical reactor was loaded with a mixture of methanol and paraformaldehyde, in molar ratio of about 1 mole methanol to 3 moles paraformaldehyde, and in a second preparation, methylal (dimethoxymethane) and paraformaldehyde were combined in a molar ratio of about 1 mole methylal to about 5 moles paraformaldehyde. In the second procedure, a small amount of formic acid, about 0.1 percent by weight of the total reactants, was added as a catalyst. The same temperatures, pressures and reaction times are maintained as in the first. Disadvantages of these products include the presence of formic acid and thermal instability of methoxy-terminated poly-oxymethylenes under ambient pressure and acidic conditions.

There is, therefore, a present need for catalytic processes to prepare oxygenated organic compounds, particularly polyoxymethylene dimethyl ethers, which do not have the above disadvantages. An improved process should be carried out advantageously in the liquid phase using a suitable condensation-promoting catalyst system, preferably a molecular sieve based catalyst which provides improved conversion and yield. Such an improved process which converts lower value compounds to higher polyoxymethylene dimethyl ethers would be particularly advantageous. Dimethyl ether is, for example, less expensive to produce than methanol on a methanol equivalent basis, and its condensation to polyoxymethylene dimethyl ethers does not produce water as a co-product.

The base diesel fuel, when blended with such mixtures in a volume ratio of from about 2 to about 5 parts diesel fuel to 1 part of the total mixture, is said to provide a higher quality fuel having significantly improved lubricity and reduced smoke formation without degradation of the cetane number or smoke formation characteristics as compared to the base diesel fuel.

This invention is directed to overcoming the problems set forth above in order to provide Diesel fuel having improved qualities. It is desirable to have a method of producing a high quality diesel fuel that has better fuel lubricity than conventional low-sulfur, low-aromatics diesel fuels, yet has comparable ignition quality and smoke generation characteristics. It is also desirable to have a method of producing such fuel which contains an additional blended component that is soluble in diesel fuel and has no carbon-to-carbon bonds. Furthermore, it is desirable to have such a fuel wherein the concentration of gums and other undesirable products is reduced.

SUMMARY OF THE INVENTION

Economical processes are disclosed for production of a mixture of oxygenated organic compounds which are suitable components for blending into fuel having improved qualities for use in compression ignition internal combustion engines (diesel engines).

According to the present invention, there is now provided a continuous process for catalytic production of oxygenated organic compounds, particularly polyoxymethylene dimethyl ethers. More specifically, continuous processes of this invention include contacting a source of formaldehyde and a predominately dimethyl ether feedstream comprising dimethyl ether and methanol with a condensation promoting catalyst capable of hydrating dimethyl ether, in a form which is heterogeneous to the feedstream, under conditions of reaction sufficient to form an effluent of the condensation comprising water, methanol, formaldehyde, dimethyl ether, one or more polyoxymethylene dimethyl ethers having a structure represented by the type formula $CH_3O(CH_2O)_nCH_3$ in which formula n is a number from 1 to about 10.

For this aspect of the invention, suitable condensation-promoting catalysts include at least one member of the group consisting of molecular sieves. A preferred class of molecular sieve is crystalline metallosilicates exhibiting the MFI crystal structure, such as crystalline aluminosilicates and crystalline borosilicates. More preferably the molecular sieve is crystalline aluminosilicate exhibiting the MFI crystal structure with a silicon-to-aluminum atomic ratio of at least 10, or the molecular sieve is crystalline borosilicate exhibiting the MFI crystal structure, and has the following compositions in terms of mole ratios of oxides:

$$0.9 \pm 0.2\ M_{2/n}O:B_2O_3:YSiO_2:ZH_2O,$$

wherein M is at least one cation having a valence of n, Y is between 4 and about 600, and Z is between 0 and about 160.0.

In another aspect, this invention provides continuous processes which further comprise fractionating the effluent of the condensation to obtain an overhead stream which is predominantly dimethyl ether, and an essentially dimethyl ether-free bottom stream comprising formaldehyde, methanol and at least methylal. Preferably at least a portion of the overhead stream containing dimethyl ether is recycled to contacting with the condensation-promoting catalyst.

According to a further aspect of this invention, the essentially dimethyl ether-free bottom stream comprising formaldehyde, methanol and at least methylal is heated with an acidic catalyst, which is heterogeneous to the feedstream, under conditions of reaction sufficient to convert formaldehyde and methanol present to methylal and higher polyoxymethylene dimethyl ethers.

Preferably, the heating of the bottom stream with the acidic catalyst employs at least one catalytic distillation column with internal and/or external stages of contact with the acidic catalyst, and internal zones to separate the methylal from the higher polyoxymethylene dimethyl ethers.

Suitable acidic catalysts include at least one member of the group consisting of bentonites, montmorillonites, cation-exchange resins, and sulfonated fluoroalkylene resin derivatives, preferably comprises a sulfonated tetrafluoroethylene resin derivative. A preferred class of acidic catalysts comprises at least one cation-exchange resin of the group consisting of styrene-divinylbenzene copolymers, acrylic acid-divinylbenzene copolymers, and methacrylic acid-divinylbenzene copolymers. Preferably, the heating of the bottom stream with the acidic catalyst employs at least one distillation column with internal and/or external stages of contact with the acidic catalyst.

Advantageously, the mixture of polyoxymethylene dimethyl ethers is contacted with an anion exchange resin to form an essentially acid-free mixture. Contacting with the anion exchange resin is preferably carried out within a section of the catalytic distillation column below the stages of contact with the acidic catalyst to form an essentially acid-free mixture.

In a preferred embodiment of the invention the essentially acid-free mixture of polyoxymethylene dimethyl ethers is fractionated within a section of the distillation column below the stages of contact with the acidic catalyst to provide an aqueous side-stream which is withdrawn from the distillation column, and an essentially water-free mixture of higher molecular weight polyoxymethylene dimethyl ethers (values of n greater 1) which is withdrawn from the distillation column near its bottom. Advantageously, at least a portion of the aqueous side-stream is used for recovery of an aqueous formaldehyde solution in an adsorption column.

In another aspect this invention is an integrated process wherein the source of formaldehyde is formed by a process comprising continuously contacting dimethyl ether in the vapor phase with a catalytically effective amount of a catalyst consisting of copper, zinc and a member selected from the group consisting of sulfur, selenium and tellurium as catalyst components at elevated temperatures to form a gaseous dehydrogenation mixture comprising formaldehyde, dimethyl ether, dihydrogen and carbon monoxide; cooling the gaseous dehydrogenation mixture with an adsorption liquid and adsorbing formaldehyde therein; and separating the resulting liquid source of formaldehyde from a gaseous mixture comprising dihydrogen and carbon monoxide.

Preferably the resulting liquid source of formaldehyde contains about 30 to about 85 percent by weight formaldehyde in methanol solution containing less than 5 percent water, and is recovered by using at least one continuous adsorption column with cooling to temperatures in a range downward from about 100° C. to 25° C.

For a more complete understanding of the present invention, reference should now be made to the embodiments illustrated in greater detail in the accompanying drawing and described below by way of examples of the invention.

GENERAL DESCRIPTION

Figure 1:
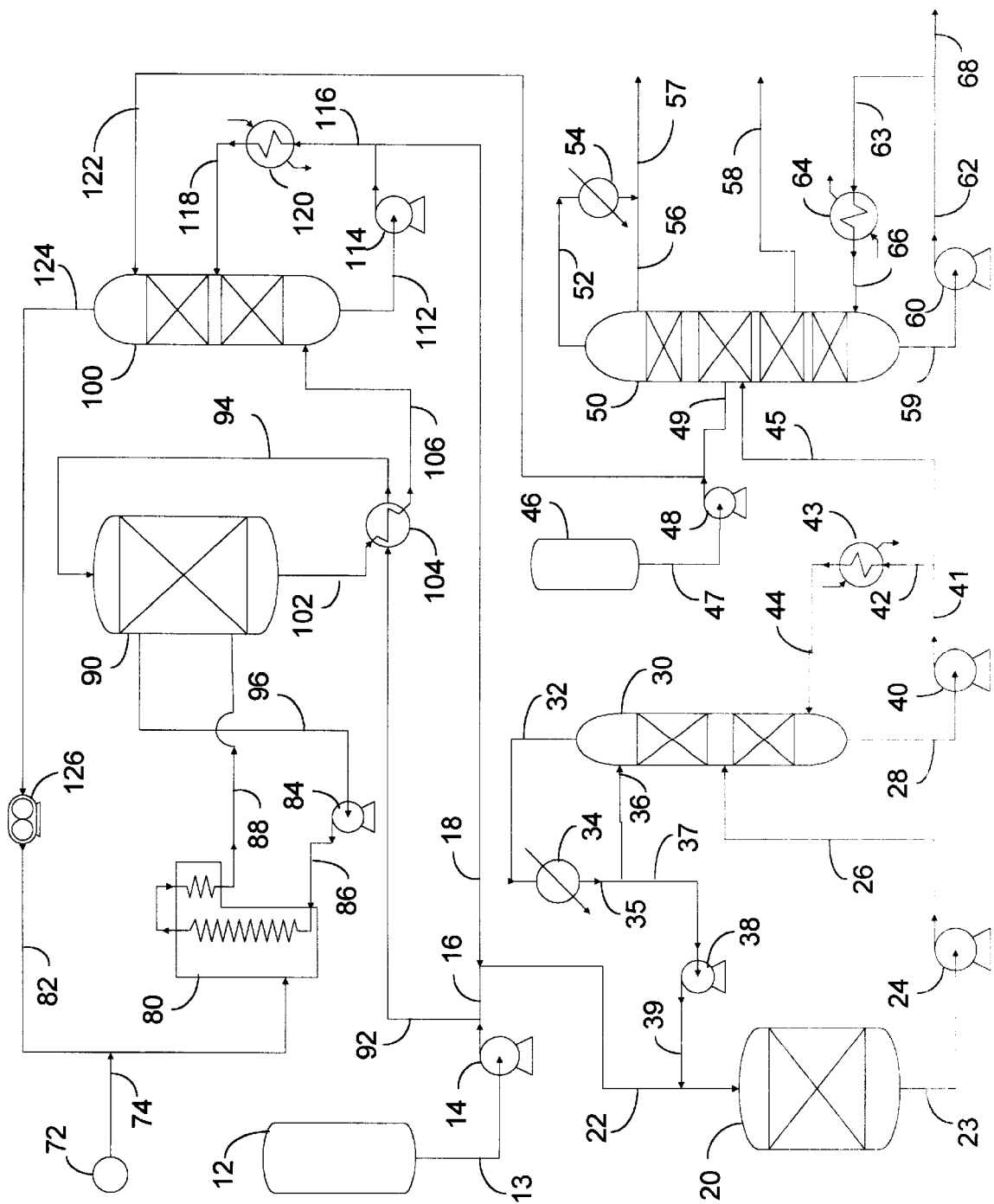
FIG. 1 is a schematic flow diagram depicting a preferred aspect of the present invention for continuous catalytic production of polyoxymethylene dimethyl ethers by chemical conversion of dimethyl ether and formaldehyde in which unreacted dimethyl ether is recovered from the effluent for recycling, and a resulting dimethyl ether-free liquid mixture is heated in a catalytic distillation column with internal stages of contact to convert formaldehyde and methanol present to methylal and higher polyoxymethylene dimethyl ethers. This reaction mixture is contacted with an anion exchange resin to form an essentially acid-free product mixture and fractionated to provide suitable components for blending into diesel fuel. The source of formaldehyde in the integrated process depicted in FIG. 1 is a stream of formaldehyde in methanol derived from dehydrogenation of dimethyl ether.

The improved processes of the present invention employ a heterogeneous, condensation promoting catalyst capable of hydrating dimethyl ether in conversion of dimethyl ether and formaldehyde to form a condensation effluent. In general, after the feedstream is passed over the catalyst it will contain a mixture of organic oxygenates at least one of which is of higher molecular weight than the starting dimethyl ether. For example, effluent mixtures can comprise water, methanol, formaldehyde, dimethyl ether, methylal and other polyoxymethylene dimethyl ethers having a structure represented by the type formula $$CH_3O(CH_2O)_nCH_3$$

in which formula n is a number ranging between 1 and about 15, preferably between 1 and about 10. More preferably the mixture contains a plurality of polyoxymethylene dimethyl ethers having values of n in a range from 2 to about 7. Conditions of reaction include temperatures in a range from about 50° to about 300° C., preferably in a range from about 1500 to about 250° C.

Stoichiometry of this condensation may be expressed by the following equations;

$$CH_3OCH_3 + n\ CH_2O \rightarrow CH_3O(CH_2O)_nCH_3$$

$$2CH_3OH + m\ CH_2O \rightarrow CH_3O(CH_2O)_mCH_3 + H_2O$$

which may be combined as in the following equation when n is equal to m;

$$CH_3OCH_3 + 2CH_3OH + 2nCH_2O \rightarrow 2CH_3O(CH_2O)_nCH_3 + H_2O$$

As shown above, the synthesis of methylal and higher polyoxymethylene dimethyl ethers from dimethyl ether, methanol, and formaldehyde is a reversible reaction that yields water as a co-product. Under certain conditions at least a portion of the water may be consumed in a dehydrogenation reaction expressed by the following equations;

$$CH_3OCH_3 + CH_3OH + H_2O \rightarrow 3CH_2O + 3H_2$$

and $$CH_3OCH_3 + H_2O \leftarrow \rightarrow 2CH_3OH$$

Sources of dimethyl ether useful herein are predominantly dimethyl ether, preferably at least about 80 percent dimethyl ether by weight, and more preferably about 90 percent dimethyl ether by weight. Suitable dimethyl ether sources may contain other oxygen containing compounds such as alkanol and/or water, preferably not more than about 20 percent methanol and/or water by weight, and more preferably not more than about 15 percent methanol and/or water by weight.

According to the present invention, the ratio of formaldehyde to dimethyl ether in the feedstreams is any mole ratio which results in the production of the desired oxygenated organic compound. The ratio of formaldehyde to dimethyl ether is preferably between about 10:1 and about 1:10 moles. The ratio of formaldehyde to dimethyl ether is preferably between about 5:1 and about 1:5 moles. More preferably, the ratio of formaldehyde to dimethyl ether is between about 2:1 and about 1:2 moles.

The process can be performed at any temperature and pressure at which the reaction proceeds. Preferred temperatures are between about 20° and about 150° C., with between about 90° and about 125° C. being more preferred. The most preferred temperatures are between about 115° and about 125° C.

The pressure can be atmospheric or super-atmospheric pressure. Preferred pressures are, according to the present invention, between about 1 and about 100 atmospheres, with between about 15 and about 25 atmospheres being most preferred.

The reaction mixture feed gas flow rate, expressed as gas hourly space velocity, can be between about 50 and about 50,000 hr$^{-1}$, most preferably, between about 100 and about 2,000 hr$^{-1}$. Un-converted dimethyl ether can be recovered from the mixture by methods well known in the art. One particularly desirable method is the use of distillation of the condensed product.

The process of this invention can be performed in either a fixed or fluid bed reactor, using either continuous or batch processing methods. It is preferred to use a fixed bed reactor and a continuous mode of operation.

Broadly, according to the present invention, a catalyst system is provided which comprises at least one molecular sieve, preferably a crystalline metallosilicate exhibiting the MFI crystal structure. Generally the crystalline metallosilicate is combined with active or inactive materials, synthetic or naturally occurring zeolites, as well as inorganic or organic materials which would be useful for binding the crystalline metallosilicate. Other well-known materials include mixtures of silica, silica-alumina, alumina sols, clays, such as bentonite or kaolin, or other binders well known in the art. The crystalline metallosilicate can also be mixed intimately with porous matrix materials, such as silica-magnesia, silica-alumina, silica-thoria, or silica-titania. The crystalline metallosilicate content can vary anywhere from a few up to 100 percent by weight of the total finished product. Typical catalytic compositions contain about 5 percent to about 80 percent by weight of the crystalline metallosilicate Generally, the term "molecular sieve" includes a wide variety of positive ion-containing crystalline materials of both natural and synthetic varieties. They are generally characterized as crystalline aluminosilicates, although other crystalline materials are included in the broad definition. The crystalline aluminosilicates are made up of networks of tetrahedra of $SiO_4$ and $AlO_4$ moieties in which the silicon and aluminum atoms are cross-linked by the sharing of oxygen atoms. The electrovalence of the aluminum atom is balanced by the use of positive ions such as alkali metal or alkaline earth metal cations.

Zeolitic materials useful herein, both natural and synthetic, have been demonstrated in the past to have catalytic capabilities for many hydrocarbon processes. Zeolitic materials, often referred to as molecular sieves, are ordered porous crystalline aluminosilicates having a definite structure with large and small cavities interconnected by channels. The cavities and channels throughout the crystalline material are generally uniform in size allowing selective separation of hydrocarbons. Consequently, these materials in many instances have come to be classified in the art as molecular sieves and are utilized, in addition to the selective adsorptive processes, for certain catalytic properties. The catalytic properties of these materials are also affected, to some extent, by the size of the molecules which are allowed selectively to penetrate the crystal structure, presumably to be contacted with active catalytic sites within the ordered structure of these materials.

Manufacture of the ZSM materials utilizes a mixed base system in which sodium aluminate and a silicon-containing material are mixed together with sodium hydroxide and an organic base, such as tetrapropylammonium hydroxide and tetrapropylammonium bromide, under specified reaction conditions to form the crystalline aluminosilicate.

A preferred class of useful molecular sieves, according to the present invention, are crystalline borosilicate molecular sieves disclosed in commonly assigned U.S. Pat. No. 4,268,420, U.S. Pat. No. 4,269,813, U.S. Pat. No. 4,292,457, and U.S. Pat. No. 4,292,458 to Marvin R. Klotz, which are incorporated herein by reference.

Suitable for use according to the present invention are, broadly, crystalline borosilicates which comprise a molecular sieve material having the following compositions in terms of mole ratios of oxides:

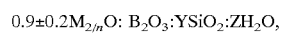

where M is at least one cation having a valence of n, Y is between 4 and about 600, and Z is between 0 and about 160.

Embodiments of such borosilicate provide an X-ray diffraction pattern comprising the following X-ray diffraction lines:

| d (Å) | Assigned Strength |
|---|---|
| 11.2 ± 0.2 | W-VS |
| 10.0 ± 0.2 | W-MS |
| 5.97 ± 0.07 | W-M |
| 3.82 ± 0.05 | VS |
| 3.70 ± 0.05 | MS |
| 3.62 ± 0.05 | M-MS |
| 2.97 ± 0.02 | W-M |
| 1.99 ± 0.02 | VW-M | wherein the assigned strengths correspond to the following values of relative peak heights:

| Assigned Strength | Relative Peak Height |
|---|---|
| VW | less than 10 |
| W | 10–19 |
| M | 20–39 |
| MS | 40–70 |
| VS | greater than 70 | and "d" represents interplanar spacings, expressed in terms of Angstrom units. A range of assigned strengths comprises all strengths between the limits shown.

Embodiments of these borosilicates are prepared by the method which comprises: (1) preparing a mixture containing an oxide of silicon, an oxide of boron, a hydroxide of an alkali metal or an alkaline earth metal, an alkyl ammonium cation or a precursor of an alkyl ammonium cation, and water; and (2) maintaining said mixture at suitable reaction conditions to effect formation of said borosilicate, said reaction conditions comprising a reaction temperature within the range of about 25° to about 300° C., a pressure of at least the vapor pressure of water at the reaction temperature, and a reaction time that is sufficient to effect crystallization.

After recovering a dimethyl ether-free mixture form the condensation effluent, the mixture is heated in a catalytic distillation column with an acidic catalyst, which is heterogeneous to the feedstream, under conditions of reaction sufficient to convert formaldehyde and methanol present to methylal and higher polyoxymethylene dimethyl ethers. Examples of the solid acidic catalyst for use in the present invention include cation exchange resins, sulfonated fluoroalkylene resin derivatives, and crystalline aluminosilicates.

Cation exchange resins that can be used in the present invention may be carboxylated or sulfonated derivatives, but sulfonated derivatives are preferred because of the high reaction yield that can be attained. Ion exchange resins that can be used may be gel-type cation exchange resins or macroporous (macroreticular) cation-exchange resins, but the latter as exemplified by Amberlite 200C of Organc Co, Ltd. and Lewalit SP112 of Bayer A.G. are preferred because of the high reaction yield that can be attained. Specific examples of useful ion exchange resins include a styrene-divinylbenzene copolymer, an acrylic acid-divinylbenzene copolymer, a methacrylic acid-divinylbenzene copolymer, etc.

A sulfonated tetrafluoroethylene resin derivative (trade name, Naflon H) is preferably used as a sulfonated fluoroalkylene resin derivative.

The most desirable of these solid acidic catalysts are macroreticular cation exchange resins having sulfonate groups.

According to an integrated process of the invention a source of formaldehyde is formed by subjecting dimethyl ether in the vapor phase to hydration and dehydrogenation in the presence a catalytically effective amount of a catalyst consisting of copper, zinc and a member selected from the group consisting of sulfur, selenium and tellurium as catalyst components at elevated temperatures to form a gaseous dehydrogenation mixture comprising formaldehyde, dimethyl ether, dihydrogen and carbon monoxide; cooling the gaseous dehydrogenation mixture to predominantly condense dimethyl ether, and adsorb formaldehyde therein; and separating the resulting liquid source of formaldehyde from a mixture comprising dihydrogen and carbon monoxide. Preferably the catalyst components copper, zinc and selenium or tellurium as catalyst components are used in an atomic ratios of 1:0.05–0.5:0.01–0.5 with the proviso that the amount zinc is at least equal to the amount of selenium or tellurium, and more preferably ratios of 1:0.05–0.5:0.05–0.4.

Preparations of suitable catalysts for conversion to formaldehyde of dimethyl according to the invention are described in, for example, U.S. Pat. No. 4,014,939, U.S. Pat. No. 4,054,609, and U.S. Pat. No. 4,354,045 which patents are specifically incorporated herein in their entirety by reference.

The catalyst used in the present invention may be prepared by any one of conventional procedures known to those skilled in the art, for example, precipitation method, thermal decomposition method, or deposition and drying method. Any of these procedures may be properly selected based on the raw material to be used.

Suitable raw materials for catalyst useful in the present invention include a copper salt of a mineral acid such as copper nitrate, copper chloride, copper sulfate, copper sulfite, copper hydroxide, copper oxide, basic copper carbonate, metallic copper, and the like as a source of copper; a zinc salt of a mineral acid such as zinc nitrate, zinc chloride, zinc sulfate, zinc sulfite, zinc hydroxide, zinc oxide, metallic zinc and the like as a source of zinc; and selenic acid, selenious acid, selenium oxide, or metallic selenium and the like as a source of selenium. Further, zinc selenide, zinc selenate, zinc selenite, and the like may be used as a source of both zinc and selenium, and copper selenide may be used as a source of both copper and selenium.

Such catalysts can be prepared for example, by kneading copper oxide with zinc oxide and tellurium dioxide (and/or selenium dioxide and/or ammonium sulfate) in the presence of water, drying the mixture at 130° C. and then pressing it to form pills, with or without admixture of a carrier. Suitable raw materials may be formed to a particle having a desired shape which may be tablet, sphere or the like and the average diameter of the particles thus formed should be more than 1 mm, preferably 2 to 5 mm. Catalyst particles are then reduced in a reductive atmosphere, for example, in two steps, first at a temperature of 100° to 300° C., preferably 150° to 250° C. for more than 0.2 hour, preferably 0.5 to 1 hour and then at the temperature of 500° to 750° C., preferably 600° to 700° C. for more than 0.1 hour, preferably 0.5 to 1 hour.

In the oxide catalyst of the type mentioned, the copper oxide is completely or partially reduced to metallic copper, during use, by the hydrogen formed on dehydrogenation of methanol. In some cases it is advantageous to reduce the catalyst prior to use, for example with gaseous hydrogen at 200° to 600° C.

The process may be carried out with the catalysts in the form of a fixed bed in the reaction vessel, for example a tubular reactor. However, a fluidized bed can also be used.

The statement that the catalysts according to the invention are capable of dehydrogenation dimethyl ether to formaldehyde is not to be taken to imply that processes according to the invention (hydration and dehydrogenation) actually proceeds via such a reaction mechanism.

In the present method, dimethyl ether may be used alone, or methanol and dimethyl ether can be used in admixture with each other to produce formaldehyde.

DESCRIPTION OF THE PREFERRED EMBODIMENTS

In order to better communicate the pre sent invention, still another preferred aspect of the invention is depicted schematically in FIG. 1. Referring now to FIG. 1, a mixture containing dimethyl ether in substantially liquid form is unloaded, for example from a road tanker (not shown), into dimethyl ether storage vessel 12 which supplies charge pump 14 through conduit 13. Charge pump 14 transfers the liquid dimethyl ether through conduit 16 into manifold 22 which is in flow communication with an inlet of catalytic reactor 20. Formaldehyde in dimethyl ether is supplied through conduit 18 to manifold 22. Catalytic reactor 20 contains a catalyst which has a condensation-promoting action and is capable of hydrating dimethyl ether. Preferred catalysts are based up on a suitable molecular sieve.

It should be apparent that effluent from the catalytic reactor is a valuable product in itself. A portion of the stream can optionally be diverted from catalytic reactor 20 for delivery to a destination (not shown) where stream may subsequently be separated to recover, for example, dimethyl ether, formaldehyde, methylal and/or other polyoxymethylene dimethyl ethers. The stream can alternatively be utilized as a source of feed stock for chemical manufacturing.

The effluent stream from catalytic reactor 20 is transferred through conduits 23 and 26, by means of pump 24, and into ether recovery column 30, where unreacted dimethyl ether is separated from the effluent stream to form a resulting liquid mixture of condensation products containing any unreacted formaldehyde. A dimethyl ether fraction is taken overhead through conduit 32 and into condenser 34 where a liquid condensate is formed. A suitable portion of the liquid condensate is refluxed into column 30 through conduits 35 and 36 while another portion of the condensate is supplied to manifold 22 through conduits 37 and 39, by means of pump 38, and into catalytic reactor 20.

Conduit 28 supplies pump 40 with liquid from the bottom of column 30. A suitable portion of the liquid stream from the bottom of column 30 is transferred through conduits 41 and 42, by means of pump 40, and into reboiler 43 which is in flow communication with the bottom of the column through conduit 44. A liquid stream from the bottom of column 30 is transferred through conduit 45 into reactive distillation column 50, where simultaneous chemical reaction and multicomponent distillation are carried out coextensively in the same high efficiency, continuous separation apparatus. Optionally, a stream containing methanol from storage vessel 46 may by fed into the reactive distillation column 50 and/or source of methanol advantageously is admixed with the bottom stream from column 30 and fed into reactive distillation column 50. Charge pump 48 transfers methanol in substantially liquid form into the reactive distillation column 50 through conduits 47 and 49.

Solid acidic catalyst is present in the reactive distillation column 50 to allow solutions containing water, methanol, formaldehyde, methylal and one or more other polyoxymethylene dimethyl ethers to be brought into solid-liquid contact counter-currently with the catalyst to form products including methylal and higher molecular weight polyoxymethylene dimethyl ethers. More volatile reaction products are taken overhead from the high efficiency separation apparatus, whereas water and less volatile reaction products are carried down the high efficiency separation apparatus.

The overhead vapor stream from reactive distillation column 50 is transferred through conduit 52 into condenser 54. A suitable portion of condensate from condenser 54 is refluxed into reactive distillation column 50 through conduits 55 and 56. A product stream containing methylal is transferred through conduit 57 to product storage (not shown). Conduit 59 supplies pump 60 with liquid containing higher molecular weight polyoxymethylene dimethyl ethers from the bottom of column 50. A suitable portion of liquid from the bottom of column 50 is transferred, by means of pump 60, through conduits 62 and 63 into reboiler 64 which is in flow communication with the bottom of the column by means of conduit 66. A product stream containing higher molecular weight polyoxymethylene dimethyl ethers is transferred through conduit 68 to product storage (not shown). Preferably, an anion exchange resin is disposed within a section of the distillation column below the stages of contact with the acidic catalyst to form an essentially acid-free mixture.

An aqueous side stream containing low levels of unreacted formaldehyde and/or methanol is discharged from column 50 through conduit 58.

In the formaldehyde preparation aspect of the invention which is described herein below, gaseous dimethyl ether is dehydrogenated in the presence of catalytically effective amount of a catalyst consisting of copper, zinc and tellurium or selenium as catalyst components. Referring now to the upper portion of FIG. 1, a mixture containing dimethyl ether in substantially liquid form is supplied from dimethyl ether storage vessel 12 to pump 14 through conduit 13. Dimethyl ether feedstream for formation of formaldehyde is transferred into formaldehyde reactor 90 through conduit 92, heat exchanger 104, and conduit 94.

Formaldehyde reactor 90 contains particulate dehydrogenation catalyst disposed in a plurality of tubes of a vertical heat exchanger which is maintained at temperatures from about 500° to 750° C. by circulation of heating fluid to the shell side of formaldehyde reactor 90 through conduit 88 from furnace 80. Heating fluid is returned to furnace 80 through conduits 96 and 86 by means of pump 84. Natural gas or other suitable fuel is supplied to furnace fuel manifold 82 through conduit 74 from fulel supply 72. As described below, at least a portion of the co-product hydrogen is used as fuel for combustion with air in furnace 80.

In this embodiment of the invention, CuZnTeO/Al$_2$O$_3$ or CuZnSeO/Al$_2$O$_3$ catalyzes the conversion of dimethyl ether to formaldehyde by a reversible dehydrogenation reaction at temperatures in a range from about 500° to 750°, preferably in a range from about 600° to 700° C.:

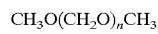

$$CH_3OCH_3 + H_2O \leftrightarrow 2CH_2O + 2H_2$$

Gaseous effluent from formaldehyde reactor 90 is transferred through conduit 102, cooled against the reactor feedstream in exchanger 104 and then passed through conduit 106 into an adsorption tower 100 where formaldehyde and dimethyl ether are separated from a mixture of gaseous co-products including hydrogen, methane, and oxides of carbon. Adsorption tower 100 contains a high efficiency packing or other means for contacting counter-currently the gaseous stream with an adsorption liquid. Formaldehyde in methanol from the bottom of the adsorption tower is circulated in a pump-around to a lower section of the tower through conduits 112 and 116, cooler 120, and conduit 118 by means of pump 114. Methanol is supplied to an upper section of the adsorption separation tower through conduit 122 by means of pump 48. Overhead temperatures are in a range of about 15° to about 55° C., preferably about 20° to about 40° C.

A gaseous overhead stream including hydrogen, methane, and oxides of carbon is transferred through conduit 124 and into furnace fuel manifold 82 by means of blower 126. Preferably the elevated temperatures are maintained in a range from about 500° to about 750° C. using a source of heat derived at least in part from this gaseous mixture, comprising dihydrogen and carbon monoxide, by combustion thereof. As needed additional fuel such as natural gas is supplied to manifold 82 from a suitable fuel source 72 through conduit 74.

As previously described, a portion of the formaldehyde in methanol solution is transferred through conduit 18 and manifold 22 into catalytic reactor 20. Formaldehyde solution from the adsorption tower is generally from about 30 to about 85 percent by weight formaldehyde in methanol solution containing less than about 5 percent water.

In view of the features and advantages of the continuous catalytic processes for direct condensation of formaldehyde and dimethyl ether to form a mixture containing methylal and higher polyoxymethylene dimethyl ethers in accordance with this invention, as compared to the known methanol condensation systems previously used, the following examples are given.

EXAMPLES 1 to 3

In Examples 1, 2 and 3 a crystalline borosilicate catalyst exhibiting the MFI crystal structure was used to convert a predominately dimethyl ether feedstream and a liquid feedstream of aqueous formaldehyde in methanol. Effluent of the condensation reactor comprised water, methanol, formaldehyde, dimethyl ether, methylal and higher polyoxymethylene dimethyl ethers having a structure represented by the type formula

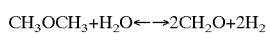

$$CH_3O(CH_2O)_nCH_3$$

in which formula n is a number from 1 to about 7.

Crystalline borosilicate molecular sieve in the form of an extrudate (1/16 inch) was calcined overnight at 500° C. The calcined extrudate was crushed and sieved to 18–40 mesh. A tubular quartz reactor was charged with 3.27 grams (5 cc) of the sieved particles. The tubular quartz reactor (approx. 10 mm inside diameter) was equipped with a quartz thermowell terminating at about the midpoint of the catalyst bed.

A liquid feed solution was prepared in a pressurized 50 mL autoclave using 11.13 grams of paraformaldehyde (95%), 15.94 grams of methanol, and 1.80 grams of water. Contents of the autoclave were stirred and heated to temperatures of 130° to 140° C. for 1 hour, and then cooled. The resulting solution was fed by a syringe pump into a preheat zone above the catalyst bed. Using mass flow controllers, a gas feed mixture of dimethyl ether and nitrogen was also fed to the top of the reactor.

Liquid products from the reactor were collected in a cool (0° C.) 25 mL flask for subsequent weighing and GC analysis. Gases exiting the collection flask were analyzed by on-line GC using both TCD and FID detectors. Samples of liquid products were collected during sampling intervals of 2 hours over an approximately 16 hour period of operation. Gas analyses were obtained by GC during each sampling interval.

Two samples were collected while temperature of the catalyst bed was controlled to three progressively higher temperatures. Each sample was about 7 grams. Operating conditions and results are summarized in Tables I, II and III.

Net conversion of the methoxy moiety (Net MeO, percent) is an indication of the conversion of groups regardless of origin, i.e., both methanol (MeOH) which has one MeO per mole and dimethyl ether (DME) which has two MeO per mol. Net MeO may be expressed as follows:

$$\text{Net MeO} = 100 \times \frac{(\text{MeOH} + 2\text{DME})_{feed} - (\text{MeOH} + 2\text{DME})_{effluent}}{(\text{MeOH} + 2\text{DME})_{feed}}$$

EXAMPLE 4

In this example an acidic catalyst was used to convert a liquid feedstream of formaldehyde in methanol under conditions which allowed gas-liquid contacting of the solid catalyst (trickle bed operation). Effluent of the condensation comprised water, methanol, formaldehyde, dimethyl ether, methylal and higher polyoxymethylene dimethyl ethers.

The acidic catalyst was a proton exchanged sulfonic acid based ion exchange resin. This polymeric material is a Bronstead (protic) acid. A tubular quartz reactor was charged with 5 cc of acidic catalyst particles. The tubular quartz reactor (approx. 10 mm inside diameter) was equipped with a quartz thermowell terminating at about the midpoint of the catalyst bed.

A liquid feed solution was prepared in a pressurized 50 mL autoclave using 7.42 grams of paraformaldehyde (95%/) and 15.93 grams of methanol. Contents of the autoclave were stirred and heated to temperatures of 130° to 140° C. for 1 hour, and then cooled. The resulting solution was fed by a syringe pump into a preheat zone above the catalyst bed. Using mass flow controllers, a gas feed mixture of dimethyl ether and nitrogen was also fed to the top of the reactor.

Liquid products from the reactor were collected in a cool (0° C.) 25 mL flask for subsequent weighing and GC analysis. Gases exiting the collection flask were analyzed by on-line GC using both TCD and FID detectors. Operating conditions and results are summarized in Table IV.

EXAMPLE 5

In this example an acidic catalyst was used to convert a mixture of formaldehyde in methanol under conditions which allowed liquid contacting of the solid catalyst. A liquid feed solution was prepared in a pressurized 50 mL autoclave using 7.4 grams of paraformaldehyde (95%) and 15.9 grams of methanol. Contents of the autoclave were stirred and heated to temperatures of 130° to 140° C. for 1 hour, and then cooled. The autoclave was opened and charged with 1.0 gram of catalyst. Contents of the autoclave were heated to reaction temperature for 2 to 3 hours with stirring. After cooling to ambient temperature and settling, the supernatant liquid was sampled for GC analysis and formaldehyde titration analysis. Results are summarized in Table V.

EXAMPLE 6

Products of several condensation runs were composited, and the composite vacuum filtered through a medium glass frit. A 90 gram aliquot of filtrate was shaken with 20 grams of basic ion-exchange resin beads (DOWEX 66) which were then allowed to settle for one hour. The resulting supernatant liquid was then gravity filtered through a medium paper filter. A suitable amount (54 grams) of molecular sieve type 3A, which had been activated by calcination at about 538° C., was mixed into the filtrate, and the mixture allowed to stand overnight at ambient temperatures. Liquid was separated from the sieve by vacuum filtration through a medium glass frit. A 45.97 gram aliquot of this acid-free, dry filtrate was charged to a small distillation apparatus consisting of a 100 mL 3-neck flask, a fractionating column and condenser. The charge was distilled into eight overhead fractions which were collected at temperature cuts according to the following schedule.

| Schedule of Overhead and Bottom Temperatures | | |
|---|---|---|
| Fraction | Temperatures, ° C. | |
| Number | Overhead | Bottom |
| 1 | 42 to 46 | 70 to 94 |
| 2 | 47 to 76 | 95 to 109 |
| 3 | 77 to 94 | 110 to 118 |
| 4 | 95 to 100 | 119 to 127 |
| 5 | 101 to 107 | 128 to 136 |
| 6 | 108 to 112 | 137 to 146 |
| 7 | 113 to 123 | 147 to 162 |
| 8 | 124 to 150 | 163 to 174 |

White solids (possibly paraformaldehyde) were observed in the column and condenser during cuts 2 through 4, but not thereafter. Composition of the distilled fraction and bottoms are given in Table VI.

EXAMPLES 7 and 8

In these Examples a catalyst of copper, zinc and selenium was used at several elevated temperatures to convert a liquid feedstream of aqueous methanol and a gaseous feedstream of dimethyl ether, nitrogen and dihydrogen. Effluent of the fixed bed reactor was a gaseous dehydrogenation mixture including formaldehyde, dimethyl ether, dihydrogen and carbon monoxide.

A tubular quartz reactor was charged with 9.27 grams (5 cc) of the CuZnSe particles which had been sieved to 18–40 mesh. The tubular quartz reactor (approx. 10 mm inside diameter) was equipped with a quartz thermowell terminating at about the midpoint of the catalyst bed.

A liquid feed solution was prepared using 13.06 grams of water and 17.33 grams of methanol. The resulting solution was fed by a syringe pump into a preheat zone above the catalyst bed. Using mass flow controllers, a gaseous feedstream of 26.9 percent by volume dimethyl ether, 6.62 volume percent nitrogen and a balance of dihydrogen was also fed to the top of the reactor.

Liquid products from the reactor were collected in a cool (0° C.) 25 mL flask for subsequent weighing and GC analysis. Gases exiting the collection flask were analyzed by on-line GC using both TCD and FID detectors. Samples of liquid products were collected during sampling intervals of 40 and 80 minutes over an approximately 6 hour period of operation. Gas analyses were obtained by GC during each sampling interval.

Samples were collected while temperature of the catalyst bed was controlled to temperatures of about 600° C. Each sample was about 2.5 or 7 grams. Operating conditions and results are summarized in Tables VII and VIII.

For the purposes of the present invention, "predominantly" is defined as more than about fifty percent. "Substantially" is defined as occurring with sufficient frequency or being present in such proportions as to measurably affect macroscopic properties of an associated compound or system. Where the frequency or proportion for such impact is not clear, substantially is to be regarded as about twenty per cent or more. The term "essentially" is defined as absolutely except that small variations which have no more than a negligible effect on macroscopic qualities and final outcome are permitted, typically up to about one percent.

TABLE I

Conversion of Feedstreams at about 100° C.
Using a Crystalline Borosilicate Catalyst Exhibiting the MFI Crystal Structure

| Temperature, ° C. | 100 | 101 |
|---|---|---|
| Run Time, min | 95 | 155 |
| Gas Feed, mol percent | | |
| Nitrogen | 32.925 | 32.925 |
| DME | 67.075 | 67.075 |
| Liquid Feed, weight percent | | |
| Methanol | 55.20 | 55.20 |
| Formaldehyde | 38.55 | 38.55 |
| Water | 6.25 | 6.25 |
| Feed Rates | | |
| Gas scc/min | 34.1 | 34.1 |
| Liquid mL/min | 0.00756 | 0.00756 |
| Conversions, mole percent | | |
| Methanol | 67.15 | 66.96 |
| DME | 4.36 | 2.71 |
| Net MeO | 28.20 | 27.10 |
| Formaldehyde | 78.84 | 78.84 |
| Selectivities, percent | | |
| Gases | | |
| CO | 0 | 0 |
| $CO_2$ | 0 | 0 |
| Liquids | | |
| Methylal | 80.548 | 78.269 |
| HPE | 0.750 | 0.751 |
| DME/MeOH | 5.38 | 5.44 |
| Carbon Balance | 92.57 | 93.39 | where MeOH is methanol, HPE is higher polyoxymethylene dimethyl ethers which are $CH_3O(CH_2O)_nCH_3$ having n greater than 1, MeO is methoxy moiety, and DME is dimethyl ether.

TABLE II

Conversion of Feedstreams at about 130° C.
Using a Crystalline Borosilicate Catalyst Exhibiting the MFI Crystal Structure

| Temperature, ° C. | 132 | 131 |
|---|---|---|
| Run Time, min | 245 | 305 |
| Gas Feed, mol percent | | |
| Nitrogen | 32.925 | 32.925 |
| DME | 67.075 | 67.075 |
| Liquid Feed, weight percent | | |
| Methanol | 55.20 | 55.20 |
| Formaldehyde | 38.55 | 38.55 |
| Water | 6.25 | 6.25 |
| Feed Rates | | |
| Gas scc/min | 34.1 | 34.1 |
| Liquid mL/min | 0.00756 | 0.00756 |

TABLE II-continued

Conversion of Feedstreams at about 130° C.
Using a Crystalline Borosilicate Catalyst Exhibiting the MFI Crystal Structure

| Conversions, mole percent | | |
|---|---|---|
| Methanol | 53.59 | 53.68 |
| DME | 5.12 | 4.75 |
| Net MeO | 23.52 | 23.33 |
| Formaldehyde | 86.71 | 86.71 |
| Selectivities, percent | | |
| Gases | | |
| CO | 0 | 0 |
| $CO_2$ | 0.095 | 0.086 |
| Liquids | | |
| Methylal | 64.480 | 64.699 |
| HPE | 0.323 | 0.326 |
| DME/MeOH | 3.48 | 3.50 |
| Carbon Balance | 91.63 | 91.53 |

Where MeOH is methanol, HPE is higher polyoxymethylene dimethyl ethers which are $CH_3O(CH_2O)_nCH_3$ having n greater than 1, MeO is methoxy moiety, and DME is dimethyl ether.

TABLE III

Conversion of Feedstreams at about 160° C.
Using a Crystalline Borosilicate Catalyst Exhibiting the MFI Crystal Structure

| Temperature, ° C. | 164 | 160 |
|---|---|---|
| Run Time, min | 345 | 400 |
| Gas Feed, mol percent | | |
| Nitrogen | 32.925 | 32.925 |
| DME | 67.075 | 67.075 |
| Liquid Feed, weight percent | | |
| Methanol | 55.20 | 55.20 |
| Formaldehyde | 38.55 | 38.55 |
| Water | 6.25 | 6.25 |
| Feed Rates | | |
| Gas scc/min | 34.1 | 34.1 |
| Liquid mL/min | 0.00756 | 0.00756 |
| Conversions, mole percent | | |
| Methanol | 34.82 | 35.19 |
| DME | 7.45 | 1.12 |
| Net MeO | 17.84 | 14.05 |
| Formaldehyde | 90.59 | 90.59 |
| Selectivities, percent | | |
| Gases | | |
| CO | 0 | 0 |
| $CO_2$ | 0.370 | 0.317 |
| Liquids | | |
| Methylal | 42.970 | 43.410 |
| HPE | 0.094 | 0.096 |
| DME/MeOH | 2.37 | 2.54 |
| Carbon Balance | 92.40 | 94.76 |

Where MeOH is methanol, HPE is higher polyoxymethylene dimethyl ethers which are $CH_3O(CH_2O)_nCH_3$ having n greater than 1, MeO is methoxy moiety, and DME is dimethyl ether.

TABLE IV

Trickle Bed Conversion of Feedstreams Using an Ion Exchange Resin Based Catalyst Exhibiting Bronstead Acid Sites

| | |
|---|---|
| Temperature, ° C. | 71 |
| Feed Rates | |
| Gas scc/min | 10 |
| Liquid mL/min | 0.0756 |
| Conversions, mole percent | |
| Methanol | 87.04 |
| Formaldehyde | 92.27 |
| Selectivities, percent | |
| Methylal | 97.78 |
| HPE | 1.77 |

Where HPE is higher polyoxymethylene dimethyl ethers which are $CH_3O(CH_2O)_nCH_3$ having n greater than 1.

TABLE V

Liquid Phase Conversion Using an Ion Exchange Resin Based Catalyst Exhibiting Bronstead Acid Sites

| | |
|---|---|
| Temperature, ° C. | 67 |
| Conversions, mole percent | |
| Methanol | 73.38 |
| Formaldehyde | 77.91 |
| Selectivities, percent | |
| Methylal | 88.20 |
| HPE | 6.03 |

TABLE VI

COMPOSITION OF OVERHEAD FRACTIONS AND BOTTOMS

| | Compound | | | | $CH_3O(CH_2O)_nCH_3$ where the value of n is: | | | | | |
|---|---|---|---|---|---|---|---|---|---|---|
| Fraction | Methylal | Methanol | Hemiacetals | Trioxane | 2 | 3 | 4 | 5 | 6 | 7 |
| Starting | 49.95 | 0.0 | 0.69 | 2.42 | 22.60 | 12.42 | 6.40 | 3.15 | 1.45 | 0.61 |
| 1 | 97.21 | 0.95 | 0.05 | 0.0 | 0.46 | 0 | 0 | 0 | 0 | 0 |
| 2 | 93.83 | 2.52 | 0.38 | 0.0 | 2.84 | 0 | 0 | 0 | 0 | 0 |
| 3 | 20.81 | 12.92 | 8.85 | 2.39 | 54.80 | 0.17 | 0 | 0 | 0 | 0 |
| 4 | 3.24 | 11.12 | 6.40 | 4.49 | 74.19 | 0.57 | 0 | 0 | 0 | 0 |
| 5 | 0.56 | 8.47 | 2.29 | 5.83 | 82.07 | 0.78 | 0 | 0 | 0 | 0 |
| 6 | 0.40 | 3.10 | 0.16 | 7.21 | 88.05 | 1.08 | 0 | 0 | 0 | 0 |
| 7 | 0.43 | 0.99 | 0.0 | 9.38 | 86.60 | 2.55 | 0.05 | 0 | 0 | 0 |
| 8 | 0.32 | 0.47 | 0.0 | 11.77 | 82.98 | 4.37 | 0.08 | 0 | 0 | 0 |
| Bottoms | 0.29 | 0.02 | 0.0 | 0.54 | 1.10 | 49.49 | 26.19 | 13.05 | 6.34 | 2.96 |

TABLE VII

Dehydrogenation of Dimethyl Ether at about 600° C. Using a Catalyst of Copper, Zinc and Selenium

| | | |
|---|---|---|
| Temperature, ° C. | 599 | 596 |
| Run Time, min | 40 | 80 |
| Gas Feed, mol percent | | |
| Nitrogen | 6.62 | 6.62 |
| DME | 26.90 | 26.90 |
| Dihydrogen | 66.48 | 66.48 |
| Liquid Feed, weight percent | | |
| Methanol | 57.03 | 57.03 |
| Water | 42.97 | 42.97 |

TABLE VII-continued

Dehydrogenation of Dimethyl Ether at about 600° C. Using a Catalyst of Copper, Zinc and Selenium

| | | |
|---|---|---|
| Feed Rates | | |
| Gas scc/min | 135 | 135 |
| Liquid mL/min | 0.07563 | 0.07563 |
| Conversions, mole percent | | |
| Methanol | 55.62 | 58.29 |
| DME | 17.33 | 14.87 |
| Net MeO | 27.75 | 26.69 |
| Selectivities, percent | | |
| CO | 3.66 | 3.27 |
| $CO_2$ | 13.94 | 15.08 |
| Formaldehyde | 66.29 | 67.15 |
| Methylal | 0 | 0 |
| HPE | 0.311 | 0.312 |
| DME/MeOH | 6.07 | 6.75 |
| Carbon Balance | 92.57 | 93.39 |

Where HPE is higher polyoxymethylene dimethyl ethers which are $CH_3O(CH_2O)_nCH_3$ having n greater than 1, MeO is methoxy moiety, and DME is dimethyl ether.

TABLE VIII

Dehydrogenation of Dimethyl Ether at about 600° C. Using a Catalyst of Copper, Zinc and Selenium

| | | |
|---|---|---|
| Temperature, ° C. | 599 | 596 |
| Run Time, min | 210 | 275 |

TABLE VIII-continued

Dehydrogenation of Dimethyl Ether at about 600° C. Using a Catalyst of Copper, Zinc and Selenium

| | | |
|---|---|---|
| Gas Feed, mol percent | | |
| Nitrogen | 6.62 | 6.62 |
| DME | 26.90 | 26.90 |
| Dihydrogen | 66.48 | 66.48 |
| Liquid Feed, weight percent | | |
| Methanol | 57.03 | 57.03 |
| Water | 42.97 | 42.97 |

TABLE VIII-continued

Dehydrogenation of Dimethyl Ether at about 600° C.
Using a Catalyst of Copper, Zinc and Selenium

| Feed Rates | | |
|---|---|---|
| Gas scc/min | 135 | 135 |
| Liquid mL/min | 0.07563 | 0.07563 |
| Conversions, mole percent | | |
| Methanol | 51.17 | 51.70 |
| DME | 13.64 | 16.33 |
| Net MeO | 23.63 | 25.95 |
| Selectivities, percent | | |
| CO | 2.78 | 2.80 |
| $CO_2$ | 15.15 | 17.31 |
| Formaldehyde | 70.63 | 68.01 |
| Methylal | 0 | 0 |
| HPE | 0.318 | 0.306 |
| DME/MeOH | 5.96 | 5.83 |

Where HPE is higher polyoxymethylene dimethyl ethers which are $CH_3O(CH_2O)_nCH_3$ having n greater than 1, MeO is methoxy moiety, and DME is dimethyl ether.

That which is claimed is:

1. A process for the catalytic production of a mixture of oxygenated organic compounds suitable as a blending component of fuel for use in compression ignition internal combustion engines, which process comprises providing a source of formaldehyde formed by the conversion of dimethyl ether in the presence of a catalyst comprising copper, zinc and a member select from the group consisting of sulfur, selenium and tellurium; and contacting the source of formaldehyde and a predominately dimethyl ether feedstream with a condensation promoting catalyst capable of hydrating dimethyl ether, in a form which is heterogeneous to the feedstream, under conditions of reaction sufficient to form an effluent of condensation mixture comprising water, methanol, formaldehyde, dimethyl ether, one or more polyoxymethylene dimethyl ethers having a structure represented by the formula
$CH_3O(CH_2O)_nCH_3$ where n is a number from 1 to about 10.

2. The process according to claim 1 wherein the conditions of reaction include temperatures in a range from about 50° to 130° C., and the condensation promoting catalyst capable of hydrating dimethyl ether comprises at least one member of the group consisting of molecular sieves.

3. The process according to claim 2 wherein the molecular sieve is crystalline metallosilicate exhibiting the MFI crystal structure.

4. The process according to claim 2 wherein the molecular sieve is crystalline aluminosilicate exhibiting the MFI crystal structure and has a silicon-to-aluminum atomic ratio of at least 10.

5. The process according to claim 2 wherein the molecular sieve is crystalline borosilicate exhibiting the MFI crystal structure, and has the following compositions in terms of mole ratios of oxides:

$0.9 \pm 0.2\ M_{2/n}O:B_2O_3:YSiO_2:ZH_2O$, wherein M is at least one cation having a valence of n, Y is between 4 and about 600, and Z is between 0 and about 160.

6. The process according to claim 2 which further comprises fractionating the effluent of the condensation to obtain an overhead stream, which is predominantly dimethyl ether, and an essentially dimethyl ether-free bottom stream comprising formaldehyde, methanol and at least methylal, and heating the bottom stream with an acidic catalyst, which is heterogeneous to the feedstream, under conditions of reaction sufficient to convert formaldehyde and methanol present to methylal and higher polyoxymethylene dimethyl ethers.

7. The process according to claim 6 wherein the heating of the bottom stream with the acidic catalyst employs at least one catalytic distillation column with internal and/or external stages of contact with the acidic catalyst, and internal zones to separate methylal from higher polyoxymethylene dimethyl ethers.

8. The process according to claim 6 wherein a source of methanol is admixed with the bottom stream, and the heating of the resulting admixture with the acidic catalyst employs at least one catalytic distillation column with internal and/or external stages of contact with the acidic catalyst, and internal zones to separate methylal from higher polyoxymethylene dimethyl ethers.

9. The process according to claim 7 wherein the mixture of polyoxymethylene dimethyl ethers is contacted with an anion-exchange resin to form an essentially acid-free mixture.

10. The process according to claim 7 wherein the mixture of polyoxymethylene dimethyl ethers is contacted with an anion-exchange resin disposed within a section of the distillation column below the stages of contact with the acidic catalyst to form an essentially acid-free mixture.

11. The process according to claim 10 wherein the essentially acid-free mixture of polyoxymethylene dimethyl ethers is fractionated within a section of the distillation column below the stages of contact with the acidic catalyst to provide an aqueous side-stream which is withdrawn from the distillation column, and an essentially water-free mixture of polyoxymethylene dimethyl ethers having values of n greater than 1 which mixture is withdrawn from the distillation column near its bottom.

12. The process according to claim 11 wherein at least a portion of the aqueous side-stream is used for recovery of an aqueous formaldehyde solution in an adsorption column.

13. The process according to claim 6 wherein the acidic catalyst comprises at least one member of the group consisting of bentonite, montmorillonite, cation-exchange resins, and sulfonated fluoroalkylene resin derivatives.

14. The process according to claim 6 wherein the acidic catalyst comprises at least one cation-exchange resin of the group consisting of styrene-divinylbenzene copolymers, acrylic acid-divinylbenzene copolymers, and methacrylic acid-divinylbenzene copolymers.

15. The process according to claim 6 wherein the acidic catalyst comprises a sulfonated tetrafluoroethylene resin derivative.

16. The process according to claim 6 wherein the at least a portion of the overhead stream containing dimethyl ether is recycled to the contacting with the condensation-promoting catalyst of claim 1.

17. The process according to claim 2 which further comprises formation of the source of formaldehyde by a process comprising continuously contacting dimethyl ether in the vapor phase with a catalytically effective amount of a catalyst consisting of copper, zinc and a member selected from the group consisting of sulfur, selenium and tellurium as catalyst components at elevated temperatures to form a gaseous dehydrogenation mixture comprising formaldehyde, dimethyl ether, dihydrogen and carbon monoxide; cooling the gaseous dehydrogenation mixture with an adsorption liquid and adsorbing formaldehyde therein; and separating the resulting liquid source of formaldehyde from a gaseous mixture comprising dihydrogen and carbon monoxide.

18. The process according to claim 17 wherein the catalyst comprises copper, zinc and selenium or tellurium as catalyst components in an atomic ratios of 1:0.05–0.5:0.01–0.5 with the proviso that the amount zinc is at least equal to the amount of selenium or tellurium present in the catalyst, and wherein the elevated temperatures are in a range from about 500° to about 750° C.

19. The process according to claim 17 wherein the catalyst comprises copper, zinc and selenium as catalyst components in an atomic ratios of 1:0.05–0.5:0.05–0.4 with the proviso that the amount zinc is at least equal to the amount of selenium present in the catalyst, and wherein the elevated temperatures are in a range from about 600° to about 700° C.

20. The process according to claim 17 wherein the resulting liquid source of formaldehyde contains about 30 to about 85 percent by weight formaldehyde in methanol solution containing less than 5 percent water by using at least one continous adsorption column with cooling to temperatures in a range downward from about 100° C. to 25° C.

21. The process according to claim 17 wherein the elevated temperatures are maintained in a range from about 600° to about 700° C. using a source of heat derived at least in part from the gaseous mixture comprising dihydrogen and carbon monoxide by combustion thereof.

* * * * *